United States Patent [19]

Prost

[11] Patent Number: 5,135,850
[45] Date of Patent: Aug. 4, 1992

[54] PROCESS FOR THE DETERMINATION BY MEANS OF FREE RADICALS OF THE ANTIOXIDANT PROPERTIES OF A LIVING ORGANISM OR A POTENTIALLY AGGRESSIVE AGE

[75] Inventor: Michel Prost, Couternon, France

[73] Assignee: Spiral Recherche et Developpment, Couternon, France

[21] Appl. No.: 576,460

[22] PCT Filed: Jan. 26, 1990

[86] PCT No.: PCT/FR90/00061
§ 371 Date: Sep. 17, 1990
§ 102(e) Date: Sep. 17, 1990

[87] PCT Pub. No.: WO90/08955
PCT Pub. Date: Aug. 9, 1990

[30] Foreign Application Priority Data

Jan. 27, 1989 [FR] France .................. 89 00999

[51] Int. Cl.$^5$ ................................. C12Q 1/02
[52] U.S. Cl. .................. 435/29; 435/240.1; 436/63
[58] Field of Search ............ 435/29, 240.1; 436/63

[56] References Cited

PUBLICATIONS

Miki Chem. Abstract #107:213235v 1987.
Oberley Cancer Research 39 pp. 1141–1149 Apr. 1, 1979.
M. Miki et al., *Archives of Biochemistry and Biophysics* 258(2):373–380 (1987).
V. N. Ushkalova et al., "Spectrophotometry, fluorometry, and kinetic methods used for analysis of blood lipid free radicals", *Chemical Abstracts*, vol. 107, No. 25, Dec. 21, 1987.
E. B. Spektor et al., "Determination of the total antioxidizing activity of the blood plasma and spinal fluid", *Chemical Abstracts*, vol. 100, No. 13, Mar. 26, 1984.
R. A. Lovstad, "The protective action of ceruloplasmin on iron (II) stimulated lysis of rat erythrocytes", *Biological Abstracts*, vol. 72, No. 9, 1981.
B. N. Ames et al., "Uric acid provides an antioxidant defense in humans against oxidant-caused and radical-caused aging and cancer: A hypothesis", *Biological Abstracts*, vol. 73, No. 12, 1982.

*Primary Examiner*—Douglas W. Robinson
*Assistant Examiner*—Jane A. Williams
*Attorney, Agent, or Firm*—Skjerven, Morrill, MacPherson, Franklin and Friel

[57] ABSTRACT

The present invention relates to a novel method of assaying or evaluating the antioxidizing activities of a living organism or a potentially aggressive agent, said method, which comprises using free radicals as a means of inducing cell lysis, being characterized in that 1) a free radical generator is brought into contact, in an appropriate liquid biological medium, with a cell material selected from the group consisting of
   (a) human, animal and plant cells,
   (b) fragments of said cells, and
   (c) synthetic walls and fragments thereof containing liposomes, said cell material having first been contaminated with a potentially aggressive agent;
2) the release of free radicals from said free radical generator is induced; and
3) the lysis of the cell material by the free radicals is evaluated by comparison with a control containing said cell material which has not been contaminated.

10 Claims, 2 Drawing Sheets

PROCESS FOR THE DETERMINATION BY MEANS OF FREE RADICALS OF THE ANTIOXIDANT PROPERTIES OF A LIVING ORGANISM OR A POTENTIALLY AGGRESSIVE AGE

FIELD OF THE INVENTION

The present invention relates to a novel method of assaying or determining the antioxidizing properties of a living organism or a potentially aggressive agent by means of free radicals.

It relates in particular to the method of evaluating on the one hand the antioxidative state of cells of a living organism, and on the other hand the oxidative or antioxidizing activities of a potentially aggressive chemical or physical agent, i.e. a chemical or physical agent capable either of increasing or accelerating or of inhibiting or retarding the cell lysis induced by free radicals.

PRIOR ART

It is known that free radicals generally have an adverse effect on the organism and in particular on the cells of this organism. Free radicals attack the cell wall at a rate which depends on the cell resistance imparted by the enzymatic and molecular equipment of said cells. When the cell wall has been degraded, perforated or opened by free radicals, the contents of the cell spread outside the wall. See the following documents in particular: Chemical Abstracts 107, 213235v, Chemical Abstracts 107, 232454g, Chemical Abstracts 100, 99345j, Biological Abstracts 72 (n° 9), page 5914, abstract n° 57169, (1981) and Biological Abstracts 73 (n° 12), page 8817, abstract n° 84420, (1982).

The abstract CA 107, 213235v, which refers to an article by M. MIKI et al., Arch. Biochem. Biophys., 258 (n° 2), pages 373-380 (1987), indicates that alphatocopherol protects rat erythrocytes from the lysis induced by free radicals.

According to the abstract CA 100,99345j cited above, which refers to an article by E. B. SPEKTOR et al., Lab. Delo (n° 1), pages 26-28 (1984), the total antioxidizing activity of a sample (blood plasma or spinal fluid) is determined by absorption at 532 nm after the induction of free radicals in a cell material (erythrocyte membranes in this particular case) by means of a UV lamp.

According to the invention, a novel technical solution is recommended whereby (i) the free radicals are not generated in said cell material, but originate from a free radical initiator added to said cell material, and (ii) the cell material has first been contaminated with a potentially aggressive agent.

SUBJECT OF THE INVENTION

According to the invention, a novel method of assaying or evaluating the antioxidizing activities of a living organism or a potentially aggressive agent is recommended, said method, which comprises using free radicals as a means of inducing cell lysis, being characterized in that 1) a free radical generator is brought into contact, in an appropriate liquid biological medium, with a cell material (I) selected from the group consisting of
  (a) human, animal and plant cells,
  (b) fragments of said cells, and
  (c) synthetic walls and fragments thereof containing liposomes, said cell material having first been contaminated with a potentially aggressive agent (II);
2) the release of free radicals from said free radical generator is induced; and
3) the lysis of the cell material by the free radicals is evaluated by comparison with a control containing said cell material which has not been contaminated.

In this method, the oxidative state of the cell material I or the influence of the agent II on said material I is assayed.

In particular, evaluation of the lysis of the cell material can be followed "kinetically" [by making measurements at regular time intervals on samples (of a constant volume) of liquid test medium containing the free radical generator, the cell material and, if appropriate, the agent II to be tested] or "non-kinetically" [by making measurements of the dose-response type on samples of the liquid test medium containing the cell material associated, if appropriate, with the agent II to be tested, and increasing aliquots of the free radical generator].

In the case of the kinetic evaluation, the resistance to free radicals of the cell material I is expressed as the time which corresponds to lysis of 50% of said cell material.

In the case of the dose-response evaluation, the resistance to free radicals of the cell material is expressed as the concentration of free radical generator which induces lysis of 50% of said cell material.

DETAILED DESCRIPTION OF THE INVENTION

Figure 1:
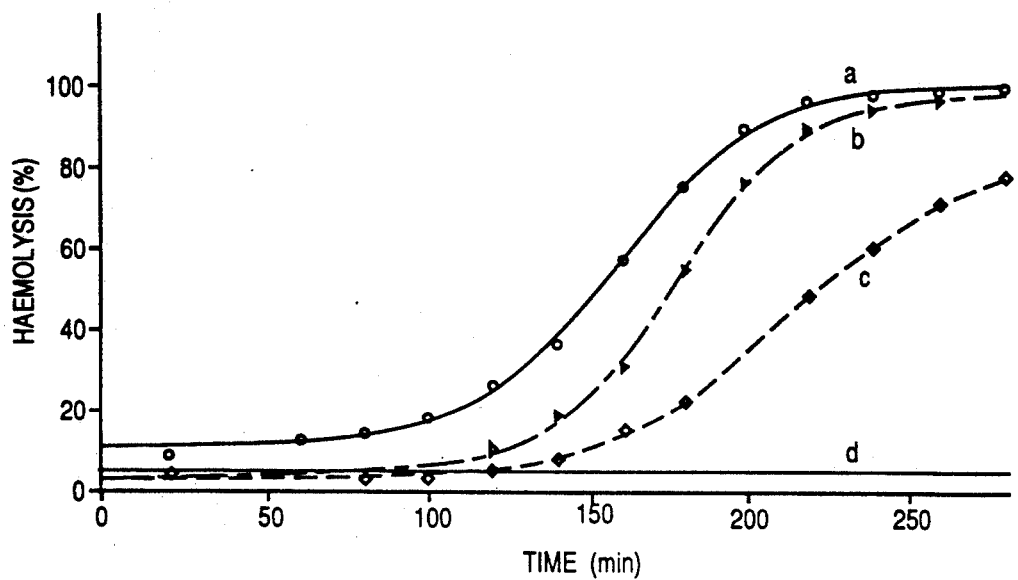

Products which release free radicals and which are commonly used in the field of polymerization to produce macromolecules may be indicated in particular among the free radical generators which are suitable according to the invention. The following may be mentioned in particular among these products: oxidizing free radical generators such as benzoyl peroxide, $C_1$-$C_8$ and preferably $C_3$-$C_4$ alkyl perbenzoates (especially n-butyl, t-butyl, i-propyl and n-propyl perbenzoates), dialkyl peroxydicarbonates in which the alkyl groups contain from 1 to 8 carbon atoms and preferably from 3 to 4 carbon atoms (especially diisopropyl peroxydicarbonate), cumene hydroxyperoxide, azo-bis(isobutyronitrile), 2,2'-azo-bis(2,4-dimethylvaleronitrile), 2,2'-azo-bis(2-amidinopropane) and, if appropriate, their addition salts such as the hydrochlorides, and analogues thereof.

The preferred oxidizing free radical generators are those which have a zero order kinetics or reaction rate (the release of free radicals is constant with time) or, preferably, 1st order kinetics or reaction rate (the release of free radicals is linear with time). The preferred oxidizing free radical generators according to the invention are on the one hand 2,2'-azo-bis(2-amidinopropane) dihydrochloride, which gives a 1st order kinetics in an aqueous medium, and on the other hand 2,2'-azo-bis(2,4-dimethylvaleronitrile), which gives a 1st order kinetics in an oily or organic liquid medium. The release of free radicals from a free radical generator is effected according to a method known per se, for example by means of heat, light (especially light of the visible spectrum or UV light), protons, electrons or X-rays; this release will preferably be initiated by photons or heat. For example, heating an aqueous solution of 2,2'-azo-bis(2-amidinopropane) dihydrochloride to a temperature of 37° C. is sufficient to trigger the release of oxidizing free radical according to the reaction

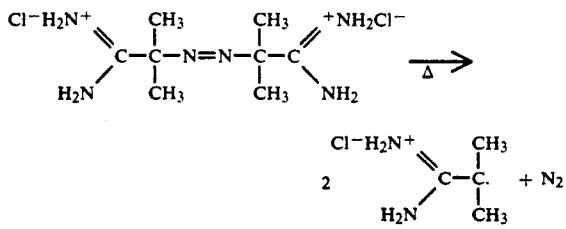

The cell material I according to the invention includes cells of human, animal, vegetable or synthetic origin or fragments of said cells, such as the walls.

It will be advantageous to use a material I containing a coloured or fluorescent marker which can be released under the action of free radicals.

Among the cell materials I which are suitable according to the invention, those which will be used in particular are pigmented living cells of human, animal or vegetable origin, i.e. living cells containing a pigment or colourant, such as haemoglobin, chlorophyll, xanthophyll, carotene and anthocyanins, whose release at the moment of cell lysis is detectable especially by measuring the variation in optical density by means of a spectrophotometer. The recommended living cells are erythrocytes of animal origin and preferably erythrocytes taken from warm-blooded animals such as mammals, in particular man. The choice of erythrocytes is based on the following factors:

blood cells such as erythrocytes have a relatively short half-life (80 days for erythrocytes of human origin);

erythrocytes possess all the molecular and enzymatic equipment for protecting against free radicals, so they are considered as representative of the other cells of the organism; and the accessibility and wide availability of erythrocytes, especially by way of a simple blood sample with a volume of a few milliliters.

When erythrocytes isolated from their plasma are subjected to oxidative-type aggression with free radicals, they apply all their enzymatic and molecular equipment to resist this aggression until the cell membrane or wall is modified thereby to the point of allowing the cell contents to escape. In the case of erythrocytes, this release of said contents can easily be determined by spectrophotometry by measuring the amount of haemoglobin which passes into the biological medium. The resistance of the erythrocyte population which is being tested is expressed either as the time taken to release 50% w/w of the haemoglobin contained in the erythrocytes (kinetic evaluation) or as the concentration of free radical generator ($CH_{50\%}$) which causes 50% haemolysis (dose-response evaluation).

The cell material can also consist of walls or wall fragments of cells, preferably of pigmented cells. The walls which are most suitable are those containing a sufficient amount of pigment or colourant which can be released at the moment of lysis by free radicals.

The cell material can also consist of a synthetic cell wall. Preferred synthetic walls are substances containing liposomes in which a coloured marker, which can be released at the moment of lysis by free radicals, is coated, fixed or immobilized. Membrane substances containing liposomes and such coloured markers are particularly advantageous in that they make it possible to avoid looking for healthy human, animal or plant subjects for the control tests, thereby ensuring a better standardization of the assay method according to the invention.

According to the invention, the cell material to be used will consist preferably of erythrocytes and most preferably of liposomes masking, coating, fixing or immobilizing a coloured marker which can be released during lysis by free radicals. In this case, the resistance to free radicals which is tested is expressed either as the 50% lysis time, i.e. the time taken to release 50% w/w of the coloured marker (kinetic measurement), or as the concentration of free radical generator which induces 50% lysis (dose-response measurement).

The expression "cell material contaminated with a potentially aggressive agent II" is understood as meaning a cell material I, as defined above, which has been brought into contact with said agent II at least 0.5 h before the method is carried out, or which has been subjected to the action of said agent II at least 0.5 h before the method of the invention is carried out.

The process of bringing said cell material I into contact with said agent II can comprise introducing the agent II into the living organism and then recovering pigmented cells contaminated with said agent II for carrying out the method of the invention. It can also comprise incorporating the agent II into cells of the material I according to a technique known per se, either by injection (according to a technology related to that of in vitro fertilization) or by osmosis.

The potentially aggressive agent II can be of a physical nature (irradiation with X-rays, beta rays, protons, etc.) or of a chemical nature (test substances or reference substances, metabolites, etc.) or even of a physicochemical nature (tobacco smoke, involving especially the release of free radicals by pyrolysis).

The biological test medium, which is an aqueous liquid medium or an organic liquid medium, comprises the cell material I contaminated with the agent II beforehand, a free radical generator and, if appropriate, one or more additives conventionally used in the field of cell cultures and biological assays, in particular a preservative. The agent II forming part of said liquid test medium is introduced either as such into said biological medium containing the cell material and the free radical generator at least 0.5 h before the release of free radicals is triggered, or already associated with said cell material after contamination. Contamination can result from the (deliberate or accidental) administration of said agent II (or one of its precursors) to the organism from which the cells are taken, or from the in vitro adsorption of said agent II by the cell membrane.

In the case of the contamination of living cells by administration to the organism, the cells carry said contaminating substance, or at least one of its metabolites, in their contents and/or on their membranes. In the case of the contamination of living or synthetic cells by adsorption, the bulk of the contaminating substance fixed is to be found in and/or on the cell wall. Contamination by adsorption is advantageously applied to lipophilic contaminating substances. Adsorption on the cell wall can be effected by incubating the cell material and the contaminating substance in an appropriate medium and at an appropriate temperature, said contaminating substance having been diluted in a selective solvent beforehand; depending on the incubation time and the concentration of the cell material used, all or (more frequently) only part of the contaminating substance in the incubation medium is fixed by adsorption to the natural or synthetic cell wall.

If the means II is a chemical substance, this can be any test substance, especially an oxidizing substance, an antioxidizing substance, a composition or association of products or else a metabolite. Among the substances which can be tested and/or assayed, it is also possible to indicate pigments (especially flavonoids), proteins, enzymes, peptides, amino acids, antibodies and antigens and, in general, any products from which antibodies can be generated. Products or means which act on the organism and/or the cells may be mentioned in particular among these substances capable of being tested and/or assayed.

To carry out the assay method according to the invention, the isolated and washed cell material is suspended in a liquid biological medium which is preferably isotonic. Incubation is carried out at a temperature within the range from 10° to 60° C., preferably from 15° to 40° C. and most preferably at a temperature of 37° C., in the presence of a free radical generator at a rate of 50 to 200 mmol/l of free radical generator for a concentration of 10 to 20% w/v of cell material.

The best mode of carrying out the method of the invention consists in suspending either a cell material consisting of erythrocytes, or synthetic wall fragments containing liposomes and a releasable coloured marker, in an isotonic physiological serum which may be buffered, and in incubating the suspension at 37° C. in the presence of 2,2'-azo-bis(2-amidinopropane) dihydrochloride at a concentration of 100 mM for a final volume of 2 ml of (preferably) aqueous liquid biological medium, or in the presence of 2,2'-azo-bis(2,4-dimethylvaleronitrile) in the same proportions for an organic biological liquid medium. The release of free radicals from the free radical generator is preferably initiated by photons and most preferably by a thermal shock (in this particular case, heating to 37° C.). Samples (0.02 ml) are taken at regular time intervals (for example every 20 minutes) until the cell residue has disappeared (this period generally being of the order of 150 to 600 minutes and especially 200-300 minutes); each sample is diluted with 1 ml of physiological serum and centrifuged [for example for 10-60 seconds at 3000-9000 g, preferably at 3000-6000 g (excessively severe centrifugation, especially above 9000 g, can upset the measurement by inducing mechanical lysis)]; an aliquot (0.2 ml) of the resulting supernatant is then transferred to the wells of a microplate or of a set of microcells for reading of the optical density by spectrophotometry (especially at 350-600 nm, irrespective of the origin of the pigmented cells or synthetic walls, and in particular at 405-410 and 540 nm when the cell material consists of erythrocytes).

In practice, the results of the variations in optical density are expressed as a percentage relative to maximum lysis of the cell material (100%). A theoretical curve adjusted at the experimental points makes it possible in particular to obtain the time corresponding to 50% lysis (this time is the longer, the better the resistance of the erythrocytes or synthetic walls to the in vitro oxidative stress applied under the abovementioned operating conditions), the slope of the sigmoid curve of the peak and the latency time (determined by the tangent to the point of inflexion of said sigmoid curve).

The kinetic evaluation described above can be replaced with an evaluation of the dose-response type.

The assay method according to the invention is very simple to carry out and can be marketed in the form of an assay kit, either for diagnostic purposes or for screening studies on various molecules and their metabolites, especially on the one hand molecules having an oxidizing or antioxidizing activity and on the other hand molecules having a long-term action. The assay method can also be carried out on human or animal plasma for the purpose of assessing the influence of said molecules on said plasma, which then constitutes said agent II in such an assay.

The method of the invention is particularly valuable for (i) assaying antimalaria agents, these generally being substances which reduce the resistance of erythrocytes and liposomes to free radicals, (ii) diagnosing diabetes, since this disease produces a hypooxidative effect in the organism, and (iii) assessing the influence of foods or food additives, especially colourants, on the organism.

This assay method has the advantage of being carried out over very short periods of time, which are preferably less than or equal to 5 h.

If liposomes are to be used as the cell material according to the invention, the following liposome preparations are recommended:

PREPARATION A:

Particles containing an association of liposomes, a coloured or fluorescent marker which can be released under the action of free radicals, and a binding means ensuring the cohesion of each particle.

PREPARATION B:

A liposome matrix consisting of an association of liposomes, a coloured or fluorescent marker which can be released under the action of free radicals, and a binding means ensuring the cohesion of the matrix.

PREPARATION C:

An inert support to which a liposome layer consisting of the matrix according to Preparation B above is adhesively bound.

PREPARATION D:

An inert support having, on at least one of its faces, at least one zone coated with a coloured or fluorescent marker which can be released under the action of free radicals, said face and said zone being coated with a layer consisting of a mixture of liposomes and a binder ensuring the cohesion of said layer; here the liposome layer masks the zone coated with the coloured or fluorescent marker.

PREPARATION E:

A porous inert support containing a coloured or fluorescent marker which can be released under the action of free radicals and which has been introduced by impregnation, said support being coated with a liposome layer analogous to that of Preparation D, masking said marker.

PREPARATION F:

A liposome matrix according to Preparation D, sensitized on the surface by a chromogenic marker of a type known in the field of chromogenic peptide substrates (see especially patent document EP-A-0 280 610); under the action of free radicals, fragments or debris of liposomes containing said marker are separated from the matrix, these fragments or debris are isolated from the matrix and collected by filtration or centrifugation and said fragments or debris are then resuspended in a biological medium appropriate for developing the colouration according to a known technique (see patent document EP-A-0 280 610 cited above).

In Preparations D–E above, the coloured or fluorescent marker which can be released under the action of free radicals is physically masked by the liposome matrix, the thickness of which must be relatively small so as to allow easy access to said marker under the action of free radicals. In Preparations A–C, it is possible to have either purely physical masking of the coloured or fluorescent marker which can be released under the action of free radicals, or a more elaborate association of said marker with the liposomes, such as fixation, immobilization or sequestration.

Finally, an assay kit is recommended which comprises (i) the cell material according to the invention and (ii) if appropriate, the free radical generator and/or the liquid biological diluting media.

Further advantages and characteristics of the invention will be understood more clearly from the following description of Examples. Taken as a whole, this information in no way implies a limitation but is given by way of illustration. Examples 1–9 relate to kinetic assays and Examples 10–15 to assays of the doseresponse type.

EXAMPLE 1

To quantify the method according to the invention, the influence of the concentration of 2,2'-azo-bis(2-amidinopropane) dihydrochloride on rat erythrocytes was studied.

After removal and washing, the rat erythrocytes are suspended (haematocrit 15% w/v) in isotonic physiological serum. These erythrocytes are brought into contact with 2,2'-azo-bis(2-amidinopropane) dihydrochoride at doses of 0 mM (control), 25 mM, 50 mM and 100 mM, the final volume of the aqueous liquid biological medium being 2 ml. The release of free radicals is initiated by heating the reaction medium to 37° C. 0.02 ml samples are taken every 20 minutes for 200–240 minutes, each sample being diluted in 1 ml of physiological serum and centrifuged (15 seconds; 4000 g). An aliquot (0.2 ml) of the supernatant is then transferred to the wells of a microplate for reading of the optical density (especially at 540 nm) by spectrophotometry.

The results collated in FIG. 1 are expressed as the time (in minutes) which corresponds to a haemolysis rate of 50% ($t_{50}\%$). Curve (a) relates to the 100 mM concentration of 2,2'-azo-bis(2-amidinopropane) dihydrochloride and gives a $t_{50}\%$ value of 158 minutes; curve (b) relates to the 50 mM concentration of 2,2'-azo-bis(2-amidinopropane) dihydrochloride and gives a $t_{50}\%$ value of 176 minutes; curve (c) relates to the 25 mM concentration of 2,2'-azo-bis(2-amidinopropane) dihydrochloride and gives a t50% value of 214 minutes; curve (d) relates to the control test, i.e. the test performed in the absence of 2,2'-azo-bis(2-amidinopropane) dihydrochloride.

The results in FIG. 1 show the relationship between dose and dependence of the effect on cell lysis with respect to the free radical generating molecule.

EXAMPLE 2

The present Example concerns the effect of an antioxidant, which in this particular case is ascorbic acid.

The operating procedures described in Example 1 above are followed using an aqueous liquid biological medium (physiological serum) containing rat erythrocytes, 100 mmol/l of 2,2'-azo-bis(2-amidinopropane) dihydrochloride and 0 (absence of antioxidant) or 0.1 mmol/l of ascorbic acid, the release of free radicals being initiated 0.5 h after the ascorbic acid has been brought into contact with the erythrocytes and the free radical generator.

Figure 2:
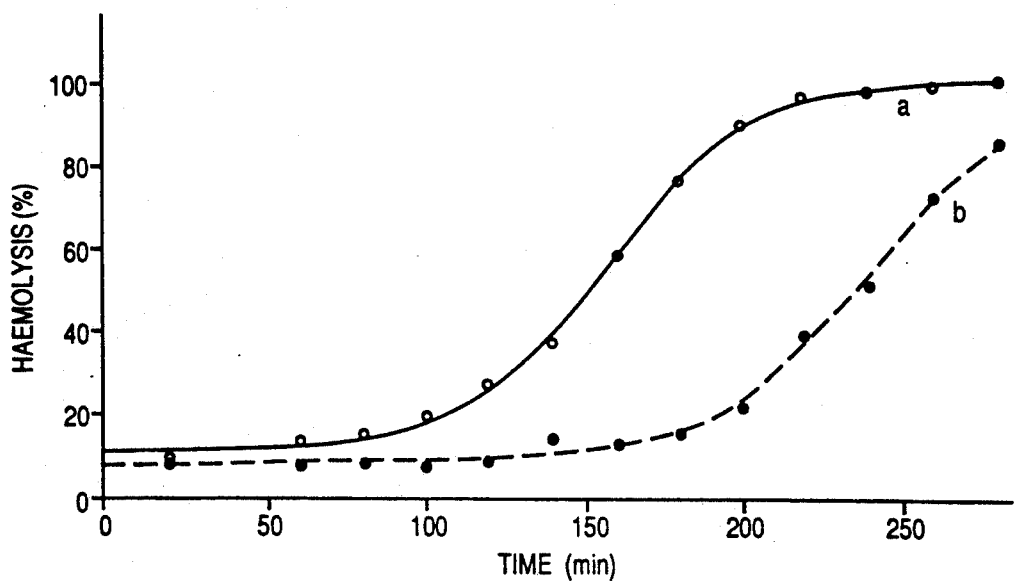

The results collated in FIG. 2 show that in the absence of ascorbic acid [curve (a)], the $t_{50}\%$ value is equal to 158 minutes and that in the presence of 0.1 mmol/l of ascorbic acid [curve (b)], the $t_{50}\%$ value is equal to 244 minutes. In other words, the presence of an antioxidant such as ascorbic acid slows down the cell lysis caused by free radicals.

EXAMPLE 3

The present Example concerns the effect of an antioxidant incorporated into the membrane of rat erythrocytes, namely butylhydroxytoluene [abbreviated to BHT; systematic nomenclature: 2,6-di(1,1-dimethylethyl)-4-methylphenol].

The operating procedures described in Example 1 are followed using healthy rat erythrocytes (control) and erythrocytes which have been preincubated beforehand at 37° C. for 0.5 h in the presence of BHT and its solvent, namely ethanol (for adsorption of the BHT on the cell membrane of the erythrocytes), and then resuspended for performing the assay. The erythrocytes treated in this way are placed in the physiological serum of Example 1 and brought into contact with 100 mmol/l of 2,2'-azo-bis(2-amidinopropane) dihydrochloride, the resulting reaction medium then being heated to 37° C.

Figure 3:
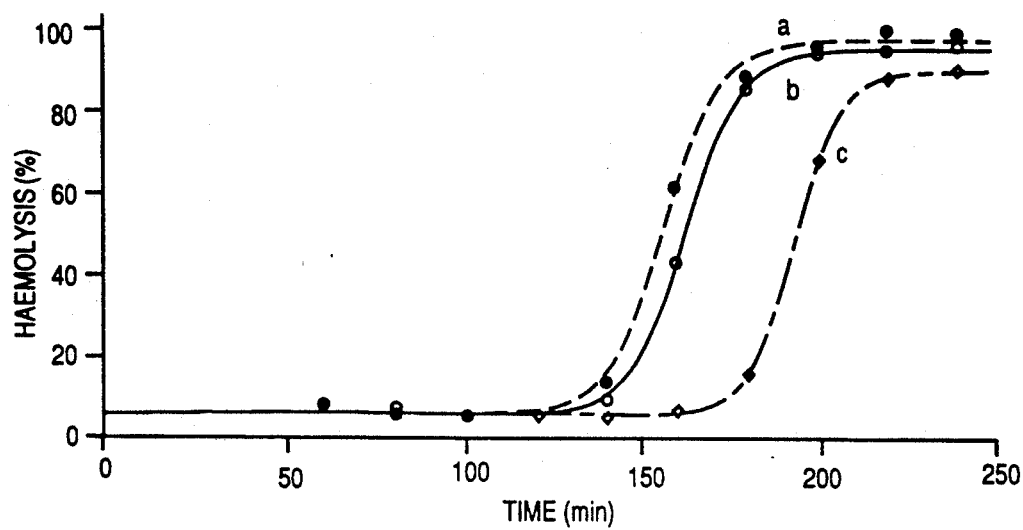

The results are collated in FIG. 3. Control curve (a) gives a $t_{50}\%$ of 163 minutes. Curve (b), which relates to the healthy rat erythrocytes which have been preincubated with the solvent for BHT, namely ethanol at a concentration of 0.5% w/v, for 0.5 h at 37° C., gives a $t_{50}\%$ value of 157 minutes. Curve (c), which relates to the same erythrocytes as curve (b), except that they have been preincubated under the same conditions with BHT and ethanol (the test medium containing 0.03 mmol/l of BHT and 0.5% w/v of ethanol), gives a $t_{50}\%$ value of 193 minutes. Comparison of curve (c) with curves (a) and (b) shows the protection which BHT provides against cell lysis. In other words, the antioxidant used here slows down the cell lysis caused by free radicals.

EXAMPLE 4

The present Example concerns the comparison of erythrocytes originating from two different subjects. After separation and washing, these erythrocytes are resuspended at the same concentration and subjected to the action of free radicals originating from a free radical generator, which in this particular case is 100 mmol/l of 2,2'-azo-bis(2-amidinopropane) dihydrochloride.

Figure 4:
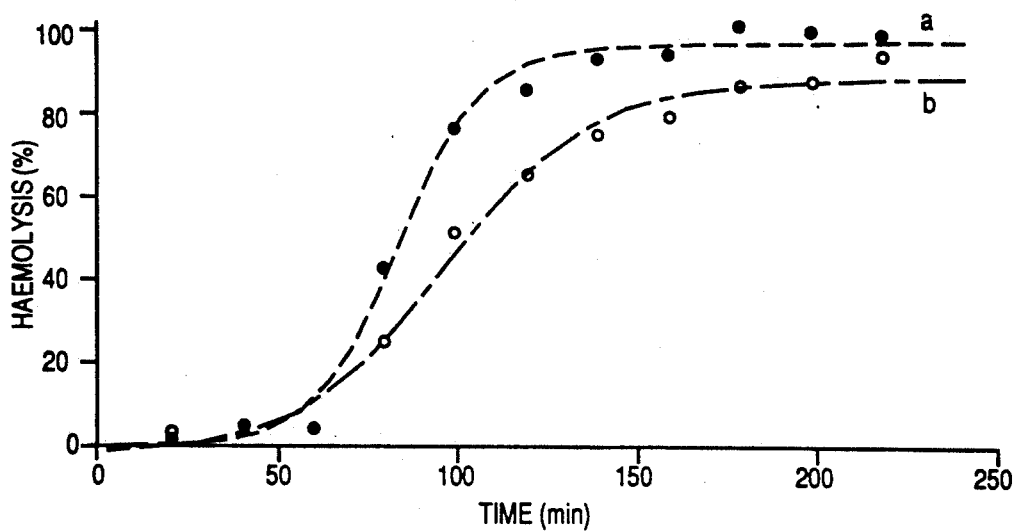

The results are collated in FIG. 4. Curve (a) shows the percentage haemolysis of erythrocytes for an adult smoker and gives a $t_{50}\%$ value of 84.4 minutes. Curve (b) shows the percentage haemolysis for an adult non-smoker and gives a $t_{50}\%$ value of 93.3 minutes. Comparison of curves (a) and (b) shows that, in smokers, the normal resistance to aggression by free radicals is lower than in subjects who are non-smokers.

EXAMPLE 5

The present Example concerns the use of plant cells for assessing the influence of irradiation on the oxidative state.

Camomile cells are divided up into two batches, one of the two batches is subjected to irradiation with a radioactive source of $3.7 \times 10^6$ Bq (100 microcuries) and the irradiated batch and non-irradiated batch are then stored under an inert atmosphere (nitrogen or argon) for 7 months. The cells of both batches are then suspended in an aqueous liquid biological medium and brought into contact with a free radical generator, namely 2,2'-azo-bis(2-amidinopropane) dihydrochloride, at 15° C. for 0.5 h. The release of free radicals is initiated by heating to 37°–40° C. and samples are then taken and analyzed according to the procedures of Example 1. The kinetic study of the lysis of the cell material shows that the cells which were irradiated beforehand have a lower resistance to free radicals than the non-irradiated cells. The corresponding curves are similar to those of FIG. 3 (the kinetics of lysis of the irradiated cells and that of lysis of the non-irradiated cells having approximately the shape of curves a and, respectively, b or c of said FIG. 3).

EXAMPLE 6

A batch of camomile seeds is irradiated with a radioactive source of $3.7 \times 10^6$ Bq and this batch is stored, together with a non-irradiated batch, for 8 months under an inert atmosphere. The irradiated and non-irradiated seeds are then ground and the resulting ground products are brought into contact with a suspension of rat erythrocytes in a physiological serum for 1 h at 15° C. The free radical generator, namely 2,2'-azo-bis(2-amidinopropane) dihydrochloride, is then introduced and the procedure indicated in Example 1 is followed. The kinetic study of the lysis of the erythrocytes in the presence of ground irradiated and non-irradiated camomile seeds gives curves approximately similar to curves a and, respectively, b or c of FIG. 3. This demonstrates that the enzymatic molecular equipment of the seeds has been modified and, in this particular case, partially destroyed by irradiation.

The present Example 6 and Example 5 above illustrate that the method of the invention makes it possible to assess the quality of foods of animal and/or vegetable origin in order to determine whether or not the food to be tested has been degraded to a greater or lesser extent before consumption.

EXAMPLE 7

The procedure indicated in Example 3 is followed, the BHT being replaced with phenothiazine. It is found that phenothiazine has an unexpected antioxidizing effect in the sense that it slows down the lysis of erythrocytes which is induced by free radicals.

EXAMPLE 8

The procedure indicated in Example 7 is followed, the erythrocytes being replaced with a synthetic cell material comprising liposomes according to Preparation C above. The antioxidizing effect of phenothiazine is observed in the same way as in Example 7.

EXAMPLE 9

A tea lyophilizate is prepared by extraction of dried leaves with water which has first been brought to the boil, and lyophilization of the resulting filtrate, one batch being subjected to irradiation with ionizing radiation (50 kGy) before lyophilization and the control batch not being irradiated. Each batch is then stored under vacuum for 9 months.

The procedure indicated in Example 3 is then followed, the BHT being replaced with the irradiated batch of tea or the non-irradiated control batch. It is found that the irradiated batch has a lower resistance to free radicals than the control batch.

EXAMPLES 10–15

Examples 10–15 below illustrate the measurement of the anti-free radical activity under assay conditions of the dose-response type.

Increasing aliquots (20 to 300 mmol) of free radical generator [2,2'-azo-bis(2-amidinopropane) hydrochloride] dissolved in an aqueous medium (water or physiological serum) are placed in tubes and then lyophilized. After resolubilization of said aliquots of free radical generator in a constant volume of test physiological serum which may or may not contain a substance to be studied, a constant amount of the cell material according to the invention is added.

The corresponding test media are incubated at 37° C. for a defined period of time (2.5 h). The effect of free radicals is then assessed by lysis of the cell material.

Example 10 was carried out with healthy rat erythrocytes and it was found that the concentration of free radical generator which induced the lysis of 50% of the erythrocytes ($CH_{50\%}$) was $108.0 \pm 20$ mmol/l.

Example 11 was carried out with the same healthy rat erythrocytes as those used in Example 10, the test medium additionally containing 10 mmol/l of mannitol. It is found that the $CH_{50\%}$ is equal to $155.6 \pm 6.1$ mmol/l, which confirms the antioxidizing effect of mannitol by comparison with the $CH_{50\%}$ of Example 10.

Example 12 was carried out with the same healthy rat erythrocytes as those used in Example 10, the test medium additionally containing an oxidizing means, namely azodicarboxylic acid bis(dimethylamide) [a compound which oxidizes thiols], at a dose of 250 mM. It is found that said peroxidizing means makes the erythrocytes more sensitive to the effect of free radicals as regards depletion of the glutathione in the erythrocytes, the $CH_{50\%}$ being reduced (compared with that of Example 10) to a value of $60.8 \pm 8.1$ mmol/l.

In Examples 13–15, similar results to those of Examples 10–12 were obtained on replacing the erythrocytes with a synthetic cell material containing liposomes according to Preparation C above.

I claim:

1. A method of assaying or evaluating the effect on lysis of a cell material which has been subjected to a chemical or physical agent comprising:
    1) a free radical generator is brought into contact, in an appropriate liquid biological medium, with a cell material selected from the group consisting of
        (a) human, animal and plant cells,
        (b) fragments of said cells, and
        (c) liposomes,
        said cell material having first been contacted with a chemical or physical agent;
    2) the release of free radicals from said free radical generator is induced; and
    3) evaluating the lysis of the cell material as compared to a control sample.

2. A method according to claim 1, wherein the cell material is selected from the group consisting of pigmented cells of human, animal or vegetable origin.

3. A method according to claim 2, wherein said pigmented cells are erythrocytes of human or animal origin.

4. A method according to claim 1, wherein the cell material is a synthetic wall fragment.

5. A method according to claim 4, wherein the cell material is a liposome material.

6. A method according to claim 1, wherein said free radical generator is selected from the group consisting of products which release free radicals according to a 0 or 1st order kinetics.

7. A method according to claim 1, wherein said free radical generator is selected from the group consisting of products which release oxidizing free radicals.

8. A method according to any one of claims 1, 6 or 7, wherein said free radical generator is 2,2'-azo-bis(2-amidinopropane) dihydrochloride.

9. A method according to claim 1, wherein 50 to 200 mmol/l of free radical generator are brought into contact with a cell material at a concentration of 10 to 20% w/v in an aqueous biological medium.

10. A method according to claim 1 or claim 9, wherein the free radicals are generated by incubation at 37° C.

* * * * *